United States Patent [19]

Goodwin

[11] Patent Number: 5,324,356

[45] Date of Patent: Jun. 28, 1994

[54] CEMENT-BASED COMPOSITIONS CONTAINING TRACER MATERIAL

[75] Inventor: Frederick R. Goodwin, Arvada, Colo.

[73] Assignee: ChemRex Inc., Milwaukee, Wis.

[21] Appl. No.: 905,126

[22] Filed: Jun. 24, 1992

Related U.S. Application Data

[63] Continuation of Ser. No. 706,935, May 29, 1991, abandoned.

[51] Int. Cl.⁵ .............................................. C04B 7/00
[52] U.S. Cl. ..................... 106/638; 106/711; 106/712; 106/741; 106/756; 106/819; 436/56; 436/174; 436/177
[58] Field of Search ............... 106/711, 712, 638, 819, 106/741, 756; 436/56, 174, 177

[56] References Cited

U.S. PATENT DOCUMENTS 4,654,165  3/1987  Eisenberg ..................... 252/408.1
4,707,453  11/1987  Wagner et al. ................. 436/501

Primary Examiner—Anthony Green
Attorney, Agent, or Firm—Michael, Best & Friedrich

[57] ABSTRACT

A tracer material having an identifiable property associated with a particular type product and/or a particular manufacturer is blended with dry, powder hydraulic cement-based building materials, which set to a hardened product after admixing with water or another hardening agent, to provide the capability of making a simple analysis of the hardened product to determine the presence or absence of the tracer material and thereby positively identify whether the building material used to produce the hardened product was a particular type and/or supplied by a particular manufacturer. The building material can be analyzed in the dry powder form prior to use to make the same type determination.

16 Claims, No Drawings

CEMENT-BASED COMPOSITIONS CONTAINING TRACER MATERIAL

This application is a continuation of Ser. No. 07/706,935 filed on May 29, 1991, now abandoned.

BACKGROUND OF THE INVENTION

This invention relates to cement-based compositions and, more particularly, to cement-based compositions used in construction and building applications.

Cement-based materials are used in a variety of building and construction applications, such a concrete, mortar, grout and concrete patching. These materials typically are a mixture a finely-ground hydraulic cement, such as Portland cement, and an aggregate and/or diluent, such as sand, and set to a hardened state after admixing with water or another hardening agent. For some applications, such materials are modified by adding latex-type materials to improve the adhesive, strength, flexibility and curing properties.

Cement-based building materials are formulated with different ingredients and/or concentration of ingredients to provide properties in the hardened product desired for a particular application(s). Thus, one material may be suitable for use as a ceramic tile grout, but completely unsuitable as a masonry mortar. During manufacture, different type building materials may be blended in the same equipment and packaged in the same type bag or carton. Many cement-based building materials have the same or substantially the same appearance to the naked eye which can lead to one type product being inadvertently introduced into the package for another type. Relatively extensive testing may be required to verify that particular type material is in the proper package. Thus, the capability of making a simple, inexpensive verification is highly desirable.

Once a cement-based building material has hardened after application, it is, at the very best, extremely difficult to positively and reliably determine the specific type of building material used or the supplier of that material. Consequently, when a manufacturer is alleged to have distributed a faulty product which caused a failed installation, it is virtually impossible for the manufacturer to verify that the correct type material was used in accordance with its specifications or recommendation or that the material in question is even one it produces.

Tracer materials have been used in a variety of processes and products to determine the presence and/or concentration of specific materials in the product. This is exemplified by U.S. Pat. Nos. 4,707,453, 4,656,049 and 4,654,165. None of these patents suggests using a tracer material in cement-based materials for the purpose and in the manner described below.

SUMMARY OF THE INVENTION

An object of the invention is to provide a simple, inexpensive method for verifying whether a hydraulic cement-based material, used to produce a hardened product, such as a building material, is a particular type or originated from a particular source.

Another object of the invention is to provide such a method which also can be used to verify the type and/or source of the material in dry powder form prior to use.

A further object of the invention is to provide a powder, hydraulic cement-based material, such as a building material, including a particulate tracer having a predetermined identifiable property which can be detected in a hardened product produced from the material to determine whether a particular type cement-based material was used or the material originated from a particular source.

A still further object of the invention is to provide such a cement-based material in which the tracer can be detected in dry powder material prior to use to determine whether the material is a particular type or originated from a particular source.

Other objects, aspects and advantages of the invention will become apparent to those skilled in the art upon reviewing the following detailed description and the appended claims.

In accordance with the invention, determination of whether a cement-base composition used to produce a hardened product was a particular type or originated from a particular source is accomplished by admixing with a powder, hydraulic cement-based composition which sets to form the hardened product after water or another hardening agent is mixed therewith, a particulate tracer material having a predetermined identifiable property associated with a particular type composition, a particular source of the composition or both. The tracer material is substantially inert in the presence of a highly alkaline pH and present in the composition in an amount to be substantially invisible to the human eye in the hardened product. When such a determination is desired, a sample of the hardened product is pulverized and at least a major part of the cementitious binder portion of the pulverized sample is removed to form a particulate residue containing the tracer material, if originally present in the composition, and the particulate residue is analyzed to determine the presence or absence of the tracer material.

In a preferred embodiment, the cementitious binder is removed by admixing with the sample a solvent capable of dissolving the cementitious binder and the tracer material is substantially insoluble in the solvent and capable of retaining its identifiable property after being exposed to the solvent.

The dry, powder composition can be analyzed prior to use determine the presence or absence of the tracer material and thereby verify the type and/or origin of the composition.

The invention also provides a cement-based composition for producing a hardened product by admixing with water or another hardening agent which composition includes a blend of a dry, powder hydraulic cement and a particulate tracer material having a predetermined identifiable property associated with a particular type composition, a particular source of the composition or both. The tracer material is substantially inert in the presence of a highly alkaline pH and present in the composition in an amount to be substantially invisible to the human eye in the composition in powder form prior to use or in the hardened product.

DESCRIPTION OF THE PREFERRED EMBODIMENTS

While the invention is adaptable for use in a wide variety of hydraulic cement-based compositions, it is particularly adaptable to cement-based building materials and will be described in connection with that application.

As used herein, the term "cement-based building materials" means a mixture of one or more hydraulic cement, and a finely divided aggregate, with or without other conventional additives, which sets to produce a hardened product after mixing with water or another suitable hardening agent such as an emulsion polymer. Suitable hydraulic cements include Portland cement, aluminate cement and mixtures thereof. The aggregate usually is sand. Suitable conventional additives include plaster of paris, latex-type materials, fibers, air entraining additives, water reducing (superplasticizers), additives set accelerating and retarding additives, shrinkage compensating agents, and water retention agents.

Representative examples of such cement-based building materials include dry set mortars, masonry mortars, latex-modified mortars, industrial grouts, ceramic tile grouts, stuccoes, concrete and masonry patching materials, self-leveling underlayments, castable refractories, screeds, cement based paints, coatings, slurries, and other conventional formulations based on a hydraulic cement and aggregate.

The tracer material has a predetermined identifiable property which can be detected and can be discriminated from other materials in the building materials by physical or chemical means. The tracer material must be substantially inert (i.e., stable) under the highly alkaline pH conditions which exist in the building material prior to use, during the setting period after water or another hardening agent has been added and in the matrix of the hardened product. The preferred identifiable properties of the tracer material include a predetermined size, shape, color, density, refractive index, reagent insolubility, fluorescence, or combination thereof. The first four properties are preferred because relatively simple techniques can be conveniently employed to determine the presence or absence of the tracer material in a hardened product.

In a preferred embodiment, a sample of the hardened product is pulverized by grinding or the like and a solvent capable of dissolving the cementitious binder portion is mixed with the sample to remove at least a major portion of the binder, leaving a particulate residue including the aggregate and the tracer material, if present in the building material used to produce the hardened product. Suitable solvents for this purpose include strong mineral acids, such as hydrochloric acid, hydrofluoric acid, sulfuric acid, nitric acid, phosphoric acid and the like. When this analytical technique is employed, the tracer material must be substantially insoluble in the solvent and capable of retaining its identifiable property or properties after being exposed to the solvent.

The particulate residue remaining after the cementitious binder has been removed can be size classified to concentrate the tracer material (if present) so it can be detected visually or with suitable detecting means. For example, a manufacturer selects a tracer material having suitable alkaline and acid resistant properties (e.g., glass), an easily identifiable and distinguishable shape (e.g., spherical beads), a particle size (e.g. 70 mesh) less than at least the majority of the aggregate and other particulate additives in the building material and a color (e.g., red) which is distinguishable from other materials in the building material and distinguishes one of the manufacturer's products (e.g., ceramic tile grout) from others. The particulate residue is screened with a screen sized to retain the red glass beads (if present) and the retained particles are visually inspected. If red glass beads are present, the manufacturer is identified as the source of the building material and the product is identified as ceramic tile grout. If no glass beads are present or the amount present is substantially smaller than that originally in the building material, the manufacturer has an objective basis for contending that the building material was produced by another manufacturer. If beads having a color other than red (e.g., green) are present and the manufacturer specified that the material identified by green beads should not be used for the application in question, the manufacturer has an objective basis for contending that the incorrect type material was used.

The cementitious binder portion can be removed by other suitable techniques, such as by heating a pulverized sample to an elevated temperature which burns off or sublimes at least a major portion of the cementitious binder. The remaining particulate residue can be analyzed in the manner described above. When this analytic technique is employed, the tracer material must be capable of retaining its identifiable property or properties after exposure to the elevated temperature used to remove the cementitious binder.

The tracer material should be substantially invisible to the human eye in the hardened product so as not to effect the overall appearance. Preferably, it also should be substantially invisible in the dry powder building material prior to use.

As will be appreciated by those skilled in the art, a wide variety of materials capable of meeting the above criteria can be used as the tracing material. Suitable tracer materials include colored and uncolored fibers, filaments, flakes, beads or particles of an inert organic or inorganic material, such as glass, quartz, sand, alumina, silicon carbide, tungsten carbide, mica, ceramic and the like and of an inert synthetic plastic, such as polyvinyl chloride, teflon, polyethylene, polypropylene, polyester, epoxy and the like. The specific type, size, color, shape and amount of tracer material depends to a large degree on the specific nature and color of the building material and the analytical technique to be used. Generally, the amount of the tracer material is about 0.01 to about 5 weight %, based on the total dry weight of the building material.

Examples of commercially-available products suitable for use as the tracer material include Colorquartz, a colored quartz typically less than ⅛ inch diameter typically marketed by 3M, Inc., a colored sand marketed by DuraFlex Corp.; Zeospheres, glass spheres marketed by 3M, Inc.; Microspheres, glass spheres marketed by Potters Industries; Polzo, colored fibers (nylon/polyester) marketed by Nurlon Corp.; and naturally colored minerals such as onyx, garnet, azurite, mica, lapis, and pyrite marketed by Agso Corp.

The tracer material also can be used to identify the type and/or origin of a building material in the dry powder form prior to use, e.g., to verify that a particular building material has been packaged in the correct bag or carton. To accomplish this, the presence or absence of the tracer material can be determined by using a suitable physical or chemical means for separating the tracer material from the dry powder. For example, a tracer material having a predetermined density can be separated by a flotation process employing a non-reactive liquid having a density intermediate to the densities of the tracer material and the remainder of the building material, the powder building material can be screened to remove particles larger or smaller than the tracer material or the cementitious binder portion of the building can be removed by dissolution with a mineral acid or other suitable solvent. Also, the presence or absence of a tracer material can be determined by examining the building material without removal of the tracer material. For example, the building material can be examined under magnification. When a fluorescent tracer material is used, selection of wave length produces an identifiable property. The building material can also be examined under polarized light for the refractive index of the tracer material.

Without further elaboration, it is believed that one skilled in the art can, using the preceding description, utilize their present invention to its fullest extent. The following examples are presented to exemplify embodiments of the invention and should not be construed as limitations thereof.

EXAMPLE 1

Different building materials made up of different blends of hydraulic cement, sand and other additives are blended by a manufacturer with the same blending equipment and packaged in similar multi-wall paper bags including a label identifying a particular product. By using a different tracer material to identify each type product in accordance with the invention, a simple analysis can be made to verify that each material is in the proper package, rather than performing extensive testing necessary to identify the differences between the properties of the different building materials.

EXAMPLE 2

A manufacturer specifies that a dry set mortar is acceptable for use on limited types of substrate (e.g., concrete, but not plywood). The dry set mortar is applied on plywood and a installation failure occurs. By using a tracer material in accordance with the invention, a simple analysis can be made to obtain positive evidence that the product was not used according to the manufacturer's recommendation.

EXAMPLE 3

A concrete patching material is reported to a manufacturer to have failed at an installation. The manufacturer suspects that another party's product was used. By using a tracer material in accordance with the invention, the manufacturer can analyze a sample of the hardened product from the failed installation and obtain positive evidence for contending that the patching material was manufactured by someone else.

From the foregoing description, one skilled in the art can easily ascertain the essential characteristics of the invention and, without departing from the spirit and scope thereof, make various changes and modifications to adapt it to different usages.

I claim:

1. A method for making a cement-based building material used in producing a hardened product identifiable as being a particular type or originated from a particular source prior to use or after hardening, said method including the steps of admixing with a powder, hydraulic cement-based building material which sets to form a hardened product after water or another hardening agent is admixed therewith, a particulate tracer material having an identifiable property associated with a particular type building material, a particular source of a building material or both which can be detected and discriminated from other components in the resulting tracer-containing building material by physical or chemical means, said tracer material being substantially inert to a highly alkaline pH and present in said building material in an amount to be invisible to the human eye in the hardened form of the product.

2. A method according to claim 1 wherein said identifiable property is a size, shape, color, density, refractive index, reagent solubility, fluorescence or combinations thereof.

3. A method according to claim 2 wherein said tracer material is selected from the group consisting of fibers, beads, flakes or particles of an inorganic material or synthetic plastic material which is inert to a highly alkaline pH.

4. A method according to claim 3 wherein the amount of said tracer material in said composition is about 0.01 to about 5 weight %, based on the total dry weight of said composition.

5. A method according to claim 1 including the further step of determining prior to use whether a building material in question is said building material, said step comprising obtaining a sample of the building material in question, and analyzing said sample to determine the presence or absence of said tracer material.

6. A method according to claim 1 including the further step of determining whether a hardened product having a cementitious portion contains said building material, said step comprising obtaining a sample of the hardened product;

pulverizing said sample of the hardened product;

removing at least a major portion of the cementitious portion of said sample to form a particular residue; and analyzing the particulate residue to determine the presence or absence of said tracer material.

7. A method according to claim 6 wherein said tracer material is selected from the group consisting of fibers, beads, flakes or particles of an inorganic material or of a synthetic plastic material which is inert to highly alkaline pH; and said method further includes the step of determining whether a hardened product having a cementitious portion contains said building material, said step comprising obtaining a sample of the hardened product, pulverizing said sample of the hardened product, removing at least a portion of the cementitious portion of said sample to form a particulate residue, and size classifying said particulate residue in a manner to concentrate particles having the size of said tracer material.

8. A method according to claim 6 wherein said tracer material is selected from the group consisting of fibers, beads, flakes or particles of an inorganic material or of a synthetic plastic material which is inert to a highly alkaline pH; and said method further includes the steps of determining prior to use whether a building material in question is said building material, said step comprising obtaining a sample of the building material in question, and size classifying the building material in question in a manner to concentrate particles having the size of said tracer material.

9. A method according to claim 8 wherein said particulate is screened and said tracer material is collected on the screen.

10. A method according to claim 6 wherein
said cementitious portion is removed by admixing with the sample a solvent which is capable of dissolving said cementitious portion, in which said tracer material is substantially insoluble and which does not substantially change said identifiable property.

11. A method according to claim 6 wherein
said cementitious portion is removed by heating the sample to an elevated temperature which is sufficient to burn off said cementitious portion, and yet does not substantially change the identifiable property of said tracer material.

12. A method according to claim 7 wherein said particulate residue is screened and said tracer material is collected on the screen.

13. A cement-based building material for producing a hardened building product by admixing with water or another hardening agent comprising a blend of
a dry powder, hydraulic cement; and
a particulate tracer material having an identifiable property associated with a particulate type building material, a particular source of a building material or both which can be detected and discriminated from other components in the resulting tracer-containing building material by physical or chemical means, said tracer material being substantially inert to a highly alkaline pH and present in said composition in an amount to be invisible to the human eye in said composition in powdered form prior to use or in the hardened product.

14. A cement-based building material according to claim 13 wherein said identifiable property is a size, shape, color, density, refractive index, reagent solubility, fluorescence or combinations thereof.

15. A method according to claim 14 wherein said tracer material is selected from the group consisting of fibers, beads, flakes or particles of an inorganic material or synthetic plastic material which is inert to a highly alkaline pH.

16. A cement-based building material according to claim 15 wherein the amount of said tracer material in said composition is about 0.01 to about 5 weight %, based on the total dry weight of said composition.

* * * * *

UNITED STATES PATENT AND TRADEMARK OFFICE
CERTIFICATE OF CORRECTION

PATENT NO. : 5,324,356
DATED : June 28, 1994
INVENTOR(S) : Fredrick R. Goodwin

It is certified that error appears in the above-indentified patent and that said Letters Patent is hereby corrected as shown below:

Column 8, line 16, delete "method", and insert ---cement-based building material---.

Signed and Sealed this

Eighteenth Day of October, 1994

Attest:

BRUCE LEHMAN

Attesting Officer

Commissioner of Patents and Trademarks